(12) United States Patent
Kim et al.

(10) Patent No.: US 11,076,759 B2
(45) Date of Patent: Aug. 3, 2021

(54) WEARABLE DEVICE AND OPERATION METHOD THEREFOR

(71) Applicant: LG INNOTEK CO., LTD., Seoul (KR)

(72) Inventors: Chul Kim, Seoul (KR); Sang Hun Lee, Seoul (KR); Jin Ho Gwon, Seoul (KR)

(73) Assignee: LG INNOTEK CO., LTD., Seoul (KR)

(*) Notice: Subject to any disclaimer, the term of this patent is extended or adjusted under 35 U.S.C. 154(b) by 339 days.

(21) Appl. No.: 16/066,260

(22) PCT Filed: Dec. 26, 2016

(86) PCT No.: PCT/KR2016/015274
§ 371 (c)(1),
(2) Date: Jun. 26, 2018

(87) PCT Pub. No.: WO2017/116100
PCT Pub. Date: Jul. 6, 2017

(65) Prior Publication Data
US 2019/0029521 A1    Jan. 31, 2019

(30) Foreign Application Priority Data

Dec. 30, 2015  (KR) .................. 10-2015-0189652

(51) Int. Cl.
*A61B 5/00* (2006.01)
*A61B 5/024* (2006.01)

(52) U.S. Cl.
CPC ........ *A61B 5/0059* (2013.01); *A61B 5/02427* (2013.01); *A61B 5/02438* (2013.01);
(Continued)

(58) Field of Classification Search
CPC .............. A61B 5/0059; A61B 5/02427; A61B 5/02438; A61B 5/681; A61B 5/7221;
(Continued)

(56) References Cited

U.S. PATENT DOCUMENTS

2005/0077360 A1* 4/2005 Ito ..................... G06K 7/10702
235/454
2007/0177223 A1* 8/2007 Kim ..................... H04N 1/1013
358/474
(Continued)

FOREIGN PATENT DOCUMENTS

| JP | 2005-211486 A | 8/2005 |
| JP | 2009-034427 A | 2/2009 |

(Continued)

OTHER PUBLICATIONS

International Search Report in International Application No. PCT/KR2016/015274, filed Dec. 26, 2016.

*Primary Examiner* — Christopher Koharski
*Assistant Examiner* — Kaitlyn E Selmer
(74) *Attorney, Agent, or Firm* — Saliwanchik, Lloyd & Eisenschenk (57) ABSTRACT

A wearable device according to an embodiment comprises: a substrate; a light-emitting unit disposed on the substrate; a light-receiving unit disposed on the substrate and spaced apart at a predetermined distance from the light-emitting unit; and a first reflection part disposed on the substrate adjacent to the light-emitting unit so as to reflect light emitted from the light-emitting unit.

8 Claims, 7 Drawing Sheets

(52) U.S. Cl.
CPC .......... *A61B 5/681* (2013.01); *A61B 5/6801* (2013.01); *A61B 5/7203* (2013.01); *A61B 5/7221* (2013.01); *A61B 5/7264* (2013.01); *A61B 5/7225* (2013.01); *A61B 2562/028* (2013.01); *A61B 2562/0233* (2013.01); *A61B 2562/0238* (2013.01)

(58) Field of Classification Search
CPC ... A61B 5/6801; A61B 5/7203; A61B 5/7264; A61B 2562/0233; A61B 5/7225; A61B 2562/0238; A61B 2562/028; A61B 5/00; A61B 5/68; A61B 5/6802
See application file for complete search history.

(56) References Cited

U.S. PATENT DOCUMENTS

| | | |
|---|---|---|
| 2007/0249916 A1 | 10/2007 | Pesach et al. |
| 2009/0036762 A1 | 2/2009 | Tateda et al. |
| 2010/0091291 A1 | 4/2010 | Wadman |
| 2010/0296777 A1* | 11/2010 | Popp .................. G02B 6/3604 385/36 |
| 2011/0087108 A1* | 4/2011 | Onoe .................. A61B 5/0261 600/473 |
| 2012/0203080 A1 | 8/2012 | Kim et al. |
| 2013/0208003 A1* | 8/2013 | Bohn .................. G02B 27/017 345/633 |
| 2014/0288435 A1* | 9/2014 | Richards ........... A61B 5/14539 600/479 |
| 2015/0341619 A1* | 11/2015 | Meir .................. G01S 17/87 348/47 |

FOREIGN PATENT DOCUMENTS

| | | |
|---|---|---|
| JP | 2009-039568 A | 2/2009 |
| JP | 2015-008995 A | 1/2015 |
| KR | 10-0997444 B1 | 11/2010 |
| KR | 10-1396146 B1 | 5/2014 |

\* cited by examiner

①: SURFACE REFLECTION (ALL NOISE FACTOR)
②: INTERNAL SCATTERING OF SKIN TISSUE (SIGNIFICANT SIGNAL)

WEARABLE DEVICE AND OPERATION METHOD THEREFOR

CROSS-REFERENCE TO RELATED APPLICATIONS

This application is the U.S. national stage application of International Patent Application No. PCT/KR2016/015274, filed Dec. 26, 2016, which claims priority to Korean Application No. 10-2015-0189652, filed Dec. 30, 2015, the disclosures of each of which are incorporated herein by reference in their entirety.

TECHNICAL FIELD

Embodiments relate to a wearable device and an operation method thereof.

BACKGROUND ART

Generally, portable terminals are following trends of higher sensitivity, smaller size and lighter weight of electronic components, bar type mobile phones have been popularized as a first generation, flip type mobile phones have been generalized as a second generation, and, currently there is a trend that flip type and third generation folder type mobile phones coexist and become universal.

In addition, a wearable device worn on a part of a human body or clothes, such as a watch type mobile phone worn on a user's wrist, has been developed.

Meanwhile, recently, according to the improvement of living standards and the development of medical technology, a trend of population aging has become remarkable worldwide. According to the population aging, prevalence of chronic diseases is increasing. As another problem of an aging society, an increasing number of elderly people living alone and dying alone caused by deterioration of an ability to support a family due to nuclear families are emerging as important social issues.

Patients with chronic diseases such as hypertension, diabetes, cerebrovascular disease, heart disease, or the like are continuously increasing. As the cause, in particular, occurrence of diseases caused by a health behavior of individuals or groups, such as diet therapy, exercise, or the like related to health, accounts for almost half or more. Therefore, it is difficult to solve these chronic diseases only with an approach based on a bio-medical model of modern medicine, and a new disease management method, that is, a health promotion approach such as elimination of health risk factors by improving lifestyle habits is required.

Therefore, recently, pulse rate measuring methods include a piezoelectric type using a piezoelectric element or the like, a magnetic type using a magnetic tunnel junction (MTJ) element, a pressing type using a film type pressure sensor, an impedance type using a bioelectrical impedance, an optical type using a light sensor, and the like. Recently, a wearable pulse measuring device capable of being worn on a wrist or a neck has been proposed.

Figure 1:
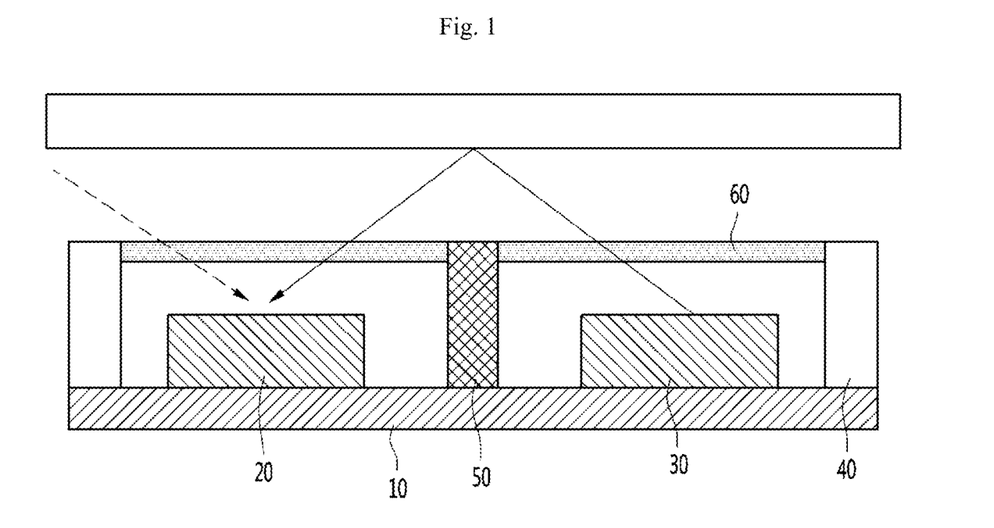
FIG. 1 is a view illustrating a wearable device according to the related art.

FIG. 1 is a view illustrating a wearable device according to the related art.

Referring to FIG. 1, a wearable device includes a substrate 10, a light emitting element 30, a light receiving element 20, a structure 40, a partition wall 50, and an optical window 60.

The substrate 10 is a base substrate for mounting components constituting the wearable device.

The light emitting element 30 generates light of a specific wavelength band according to a light emitting control signal.

The light receiving element 20 receives light incident according to light generated via the light emitting element 30.

The structure 40 is a support structure for supporting the optical window 60.

The partition wall 50 is disposed between the light emitting element 30 and the light receiving element 20 and inhibits light generated via the light emitting element 30 from being directly incident on the light receiving element 20.

The optical window 60 is disposed on an emitting surface and an incident surface of the light emitting element 30 and the light receiving element 20 respectively, and protects the light emitting element 30 and the light receiving element 20 from the outside.

The wearable device as described above detects a human body signal according to a voltage of light (that is, a light receiving voltage) received via the light receiving element 20. Here, the human body signal may include a heart rate, oxygen saturation, or the like.

Figure 2:
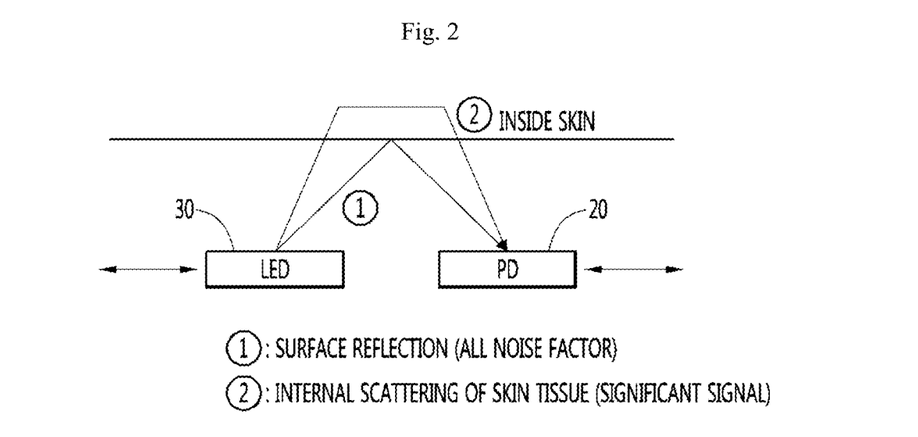
FIG. 2 is a view illustrating an operating principle of a wearable device according to the related art.

FIG. 2 is a view illustrating an operating principle of the wearable device according to the related art.

Referring to FIG. 2, light generated by the light emitting element 30 is reflected by a skin corresponding to a measurement object and is incident on the light receiving element 20.

At this point, the incident light includes first light reflected by a surface of the skin and second light reflected by internal scattering of the skin tissue inside the skin.

In addition, the first light is substantially light due to a noise factor, and the second light alone is a significant signal used for detecting the human body signal.

However, according to the related art, an interval between the light emitting element 30 and the light receiving element 20 is limited, and accordingly, there is a problem that the first light described above is generated.

In addition, according to the related art, distortion of an optical path occurs due to the limited interval, and power consumption increases for amplification of the signal, and accordingly, there is a problem that battery consumption is increased or the life span is shortened.

Further, according to the related art, it is necessary to configure a set of light receiving devices of an additional light emitting device in order to reduce the power consumption as described above, and, accordingly there is a problem that a unit price of products is raised or volumes of the products are increased.

Furthermore, according to the related art, a size of the received light varies depending on an age, and a skin color, and accordingly, there is a problem that accuracy of the detected human body signal is deteriorated according to a measurement object.

DISCLOSURE

Technical Problem

According to an embodiment of the present invention, there is provided a wearable device and an operation method thereof capable of minimizing an optical path passing through a skin tissue while reducing surface reflection by disposing a reflector for reflecting light between a light emitting element and a light receiving element.

In addition, according to an embodiment of the present invention, there is provided a wearable device and an operation method thereof capable of detecting accurately a desired a human body signal by optimizing an optical path between a light emitting element and a light receiving element.

Technical problems to be solved by the embodiments proposed herein are not limited to those mentioned above, and other unmentioned technical aspects should be clearly understood by one of ordinary skill in the art to which the embodiments proposed herein pertain from the description below.

Technical Solution

A wearable device according to an embodiment includes: a substrate; a light emitting unit disposed on the substrate; a light receiving unit disposed on the substrate and spaced a predetermined interval apart from the light emitting unit; and a first reflector disposed on the substrate adjacent to the light emitting unit and configured to reflect light generated by the light emitting unit.

In addition, the light emitting unit is disposed on the substrate such that a light emitting surface is located on a side surface thereof.

Further, the light emitting unit generates the light in a first direction parallel to a measurement object, and the first reflector reflects the light in a second direction corresponding to the measurement object.

Furthermore, the first reflector includes a micro-electro-mechanical systems mirror (MEMS mirror).

In addition, the light emitting unit is disposed on the substrate such that a light emitting surface is located on an upper surface thereof, and generates light in a first direction corresponding to the measurement object.

Further, the wearable device further includes a second reflector disposed at a location facing the light emitting surface of the light emitting unit, and the first reflector is disposed at a light reflection path of the second reflector.

Furthermore, the second reflector reflects light generated in the first direction to a second direction parallel to the measurement object, and the first reflector reflects light reflected in the second direction to a third direction corresponding to the measurement object.

In addition, the wearable device further includes an optical window disposed on the substrate and configured to protect the light emitting unit and the light receiving unit, and the second reflector is disposed at a lower surface of the optical window.

Further, the wearable device further includes a driving unit disposed on the substrate, and the light receiving unit is disposed on the driving unit.

Further, the driving unit changes a reflection angle of the first reflector within an effective range.

Further, the driving unit changes a reflection angle of the first reflector to measure a signal-to-noise ratio of an optical signal received via the light receiving unit according to each of reflection angles, and sets a reflection angle of the first reflector based on a reflection angle of the highest measured signal-to-noise ratio.

Furthermore, the driving unit sets a reflection angle of the first reflector at the time of initial wearing or re-wearing of the wearable device.

In addition, the wearable device further includes a partition wall disposed between the light emitting unit and the light receiving unit of the substrate and configured to divide an upper region of the substrate into a region in which the light emitting unit is disposed and a region in which the light receiving unit is disposed.

Meanwhile, an operation method of a wearable device according to an embodiment includes: changing a reflection angle of a reflector configured to reflect light generated in a light emitting unit in a direction of a measurement target within an effective range; determining a state of light received at the light receiving unit with respect to each of the reflection angles changed within the effective range; and determining a reflection angle of the reflector according to the determined state of the light.

In addition, the light emitting unit generates light in a first direction parallel to the measurement object, and the reflector reflects the light in a second direction corresponding to the measurement object according to the reflection angle.

Further, the determining of a state of light includes determining a signal-to-noise ratio of an optical signal received via the light receiving unit.

Furthermore, the determining includes confirming a reflection angle of the highest signal-to-noise ratio and determining the confirmed reflection angle as a reflection angle of the reflector.

Advantageous Effects

According to an embodiment of the present invention, a reflector using an optimized MEMS mirror is disposed between a light emitting element and a light receiving element, and thus noise reflected on a skin surface of a measurement object can be reduced.

In addition, according to an embodiment of the present invention, a reflector for reflecting light is disposed between a light emitting element and a light receiving element, and thus an optical path passing through a skin tissue can be minimized while reducing surface reflection.

Further, according to an embodiment of the present invention, a separate green light emitting element for measuring a heart rate can be removed by improving quality of a heartbeat signal on a wrist, and thus competitiveness of a unit price can be increased by lowering unit prices of products, and volumes of the products can be miniaturized, accordingly.

MODES OF THE INVENTION

Advantages, features, and methods of achieving the same of the present invention will become clear upon referring to embodiments described below in detail with reference to the accompanying drawings. However, the present invention is not limited to the embodiments disclosed below and may be implemented in various other forms. The embodiments are merely provided to make the disclosure of the present invention complete and completely inform one of ordinary skill in the art to which the present invention pertains of the scope of the present invention. The present invention is defined only by the scope of the claims below. Like reference numerals refer to like elements throughout the specification.

In describing embodiments of the present invention, when detailed description of a known function or configuration is deemed to unnecessarily blur the gist of the present invention, the detailed description will be omitted. Terms described below are terms defined in consideration of functions in the embodiments of the present invention and may vary depending on the intention of a user or operator or a practice. Therefore, such terms should be defined on the basis of the entire contents disclosed herein.

Combinations of blocks and steps of flowcharts in the accompanying drawings can be performed by computer program instructions. Such computer program instructions can be embedded in a processor of a general-purpose computer, a special-purpose computer, or other programmable data processing equipment. Therefore, the instructions performed by the processor of other programmable data processing equipment generate means for performing functions described in each of the blocks or each of the steps in the flowcharts in the drawings. Therefore, the instructions performed by the processor of other programmable data processing equipment generate means for performing functions described in each of the blocks or each of the steps in the flowcharts in the drawings. Because the computer program instructions can also be saved in a computer-usable or computer-readable memory capable of supporting a computer or other programmable data processing equipment to implement a function in a specific way, the instructions stored in the computer-usable or computer-readable memory can also produce a manufacturing item which incorporates an instruction means performing a function described in each of the blocks or each of the steps of the flowcharts in the drawings. Because the computer program instructions can also be embedded in a computer or other programmable data processing equipment, the instructions performed in a computer or other programmable data processing equipment by a process executed in a computer being generated by a series of operation steps being performed in the computer or other programmable data processing equipment can also provide steps for executing functions described in each of the blocks and each of the steps of the flowcharts in the drawings.

Also, each of the blocks or each of the steps may represent a module, a segment, or a part of a code including one or more executable instructions for executing a specified logical function(s). Also, it should be noted that functions mentioned in the blocks or steps can also be performed in a different order in a few alternative embodiments. For example, two blocks or steps which are consecutively illustrated can substantially be performed simultaneously, or the blocks or steps can also be performed in a reverse order sometimes according to corresponding functions.

In an embodiment according to the present invention, there is provided a wearable device and an operation method thereof capable of reducing a surface reflection noise while minimizing an optical path passing through an internal skin tissue of a measurement object by disposing reflector for reflecting light generated via the light emitting element in an adjacent region of the light emitting element.

Figure 3:
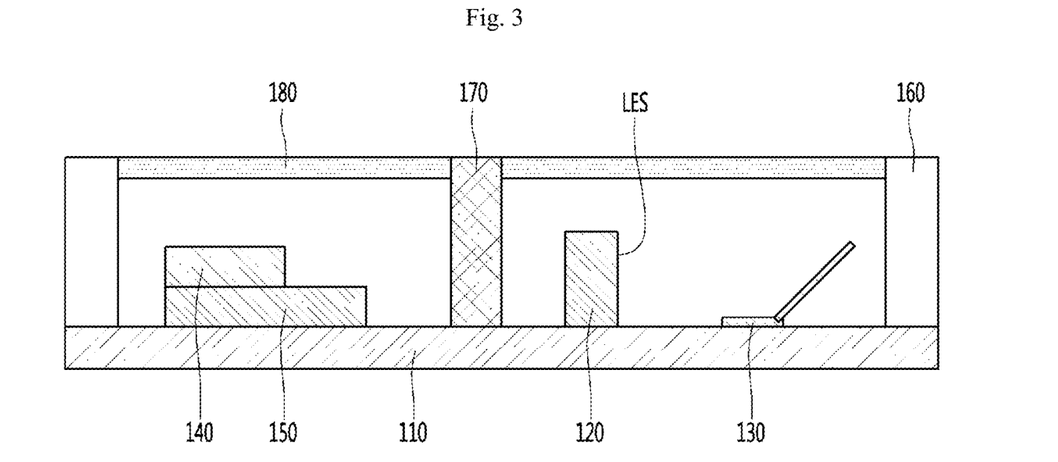
FIG. 3 is a view illustrating a structure of a wearable device according to a first embodiment of the present invention.

FIG. 3 is a view illustrating a structure of a wearable device according to a first embodiment of the present invention.

Referring to FIG. 3, a wearable device includes a substrate 110, a light emitting unit 120, a reflector 130, a light receiving unit 140, a driving unit 150, a structure 160, a partition wall 170, and an optical window 180.

The substrate 110 is a base substrate for mounting components constituting the wearable device.

That is, the substrate 110 may be a support substrate of the wearable device on which a single circuit pattern is formed and may refer to a specific insulating layer on which any one of circuit pattern of a substrate having a plurality of laminated structures is formed.

The substrate 110 may be a thermosetting or thermoplastic polymer substrate, a ceramic substrate, an organic-inorganic composition material substrate, or a fiberglass immersion substrate, and when a polymer resin is included, an epoxy-based insulating resin may be included, otherwise, a polyimide-based resin may be included.

That is, the substrate 110 is a plate on which an electrical circuit capable of changing wirings is disposed and may include all of printing, a wiring plate, and an insulating substrate which are formed of an insulating material which is able to form a conductive pattern on a surface of the insulating substrate.

The substrate 110 may be rigid or flexible. For example, the substrate 110 may include glass or plastic. Specifically, the substrate 110 may include a chemically tempered/semi-tempered glass, such as soda lime glass, aluminosilicate glass, etc., a reinforced or flexible plastic such as polyimide (PI), polyethylene terephthalate (PET), propylene glycol (PPG), polycarbonate (PC), etc., or sapphire.

In addition, the substrate 110 may include an optically isotropic film. For example, the substrate 110 may include cyclic olefin copolymer (COC), cyclic olefin polymer (COP), optically isotropic polycarbonate (PC), optically isotropic polymethylmethacrylate (PMMA), etc.

Further, the substrate 110 may partially have a curved surface and may be bent. That is, the substrate 110 may partially have a flat surface and may partially have a curved surface and may be bent. Specifically, an end portion of the substrate 110 may have a curved surface and may be bent, or, may have a surface with a random curvature and may be bent or crooked.

Furthermore, the substrate 110 may be a flexible substrate having flexible characteristics.

In addition, the substrate 110 may be a curved or bent substrate. Here, the substrate 110 may form a wiring layout for electrical wirings which connect circuit components based on a circuit design, and electrical conductors may be disposed thereon. Further, electrical components may be mounted on the substrate 110, and the substrate 110 may form wirings configured to connect the electrical components to make a circuit, and may mechanically fix the components besides functioning as electrically connecting the components.

A circuit pattern (not shown) electrically connected to the light emitting unit 120, the reflector 130, the light receiving unit 140, and the driving unit 150 to be described later is formed on a surface of the substrate 110.

The circuit pattern may be formed by a general process of manufacturing a PCB, such as an additive process, a subtractive process, a modified semi additive process (MSAP), a semi additive process (SAP), etc., and detailed descriptions thereof will be omitted herein.

The surface of the substrate 110 may be divided into a first region in which the light emitting unit 120 is mounted and a second region in which the light receiving unit 140 is mounted.

In addition, the partition wall 170 is disposed between the first and second regions, and the surface of the substrate 110 may be divided into the first region and the second region by the partition wall 170.

The partition wall 170 is disposed between the light emitting unit 120 and the light receiving unit 140 and inhibits light generated via the light emitting unit 120 from being directly incident on the light receiving unit 140.

In addition, the light emitting unit 120 and the reflector 130 are disposed in the first region of the substrate 110.

The light emitting unit 120 includes a light emitting element configured to generate light of a specific wavelength band according to a light emission control signal.

At this point, a light emitting surface (LES) of the light emitting unit 120 is disposed so as not to be overlapped with a skin of the measurement object. For this, the light emitting unit 120 is disposed to be vertically erected on the substrate 110. Accordingly, the LES of the light emitting unit 120 is not disposed on the light emitting unit 120 so as to be overlapped with the skin of the measurement object and is disposed on a side portion of the light emitting unit 120.

Therefore, the light generated by the light emitting unit 120 is not directly transmitted to the measurement object.

In other words, in a general wearable device, the light generated by the light emitting unit 120 is directly transmitted to the skin of the measurement object. For this, the light emitting unit 120 in the related art generates light in a direction perpendicular to the skin of the measurement object. That is, the LES of the light emitting unit 120 in the related art is disposed to face the skin of the measurement object.

However, the light emitting unit 120 according to the present invention does not emit light directly to the skin of the measurement object, but generates light in a direction in which the reflector 130 is disposed.

For this, the light emitting unit 120 generates light in a direction parallel to the skin of the measurement object, and the LES of the light emitting unit 120 is disposed in a direction perpendicular to the skin of the measurement object, accordingly.

The reflector 130 reflects the light generated via the light emitting unit 120 in a specific direction according to a predetermined angle.

That is, the reflector 130 includes a light reflection region, and the light reflection region is disposed to face the LES of the light emitting unit 120.

In addition, the light reflection region of the reflector 130 reflects the light generated via the light emitting unit 120 to the skin of the measurement object.

The reflector 130 is preferably a micro-electro-mechanical systems mirror (MEMS mirror).

Recently, a technology combining a small mechanical device such as a sensor valve, a gear, a reflector, and a semiconductor chip actuator with a computer, called a micro-electro-mechanical system (MEMS), has been spotlighted. The MEMS is also referred to as a "smart meter," and is a device with a microcircuit of a small silicon chip mounted when manufacturing a mechanical device such as a mirror and a sensor, which may be used in various applications such as a device for inflating an airbag to match a speed detected by a vehicle airbag and a weight of a passenger, a global positioning system sensor capable of identifying a continuous tracking and handling of freight transport, a sensor for sensing and interacting with a change of air flow according to a surface air resistance of an airplane wing, an optical switching device capable of emitting an optical signal at a speed of 20 nanoseconds, a cooling and heating device operated by a sensor, and an in-building sensor for changing flexibility of materials responding to atmospheric pressure. As described above, since the MEMS may significantly reduce the size and cost of a product to which the application is applied while greatly improving performance thereof, the MEMS has been applied in various fields.

The above-described MEMS has also been applied to implementing a mirror. The mirror implemented by the MEMS (hereinafter referred to as a "MEMS mirror") may be divided into a mirror using an electrostatic force, a mirror using an electromagnetic force, a mirror using a piezoelectric force, a mirror using thermal deformation, and the like according to a driving method for driving the mirror. The mirror using the electrostatic force may be divided again into a parallel plate driving method and a comb-driving method.

In addition, each of the driving methods has advantages and disadvantages in comparison with other driving methods. In the driving methods, the comb-driving method, which is easy to manufacture and has a low power consumption, but is excellent in driving force, torque, and maximum stroke, is most widely used.

Further, the above-described MEMS mirror may be slightly changed in angle within a predetermined effective angle range.

Accordingly, in the present invention, a reflection angle of the MEMS mirror constituting the reflector 130 is selectively changed so as to reflect the light generated via the light emitting unit 120 to an optimum optical path for the measurement object.

In addition, the light reflection region of the reflector 130 faces the LES of the light emitting unit 120. Preferably, an uppermost portion of the reflector 130 is located higher than that of the light emitting unit 120 so that the light is reflected to the measurement object without loss of the light generated via the light emitting unit 120.

The structure 160 is a support structure for supporting the optical window 180.

The optical window 180 is spaced a predetermined interval apart from the light reflection region of the reflector 130 and a light incident surface of the light receiving unit 140, and protects the light emitting unit 120, the light receiving unit 140, and the reflector 130 from the outside.

The optical window 180 forms an optical path so that light reflected via the reflector 130 is supplied to the outside (preferably, the skin of the measurement object), and allows light incident from the outside to be supplied to the light receiving unit 140.

Meanwhile, the driving unit 150 and the light receiving unit 140 are disposed in the second region of the substrate 110.

At this point, the driving unit 150 is disposed on the substrate 110, and the light receiving unit 140 is disposed on the driving unit 150.

The driving unit 150 may be a signal processing element for processing a signal received via the light receiving unit 140, and may be implemented as an application specific integrated circuit (ASIC).

The light receiving unit 140 is disposed on the driving unit 150. The light receiving unit 140 is disposed on the driving unit 150 such that the light incident surface faces to an upper portion.

Meanwhile, the driving unit 150 includes a controller (not shown), and controls the reflector 130 according to a state of wearing the wearable device, so that a reflection angle of the reflector 130 is adjusted according to a human body on which the wearable device is worn.

Figure 4:
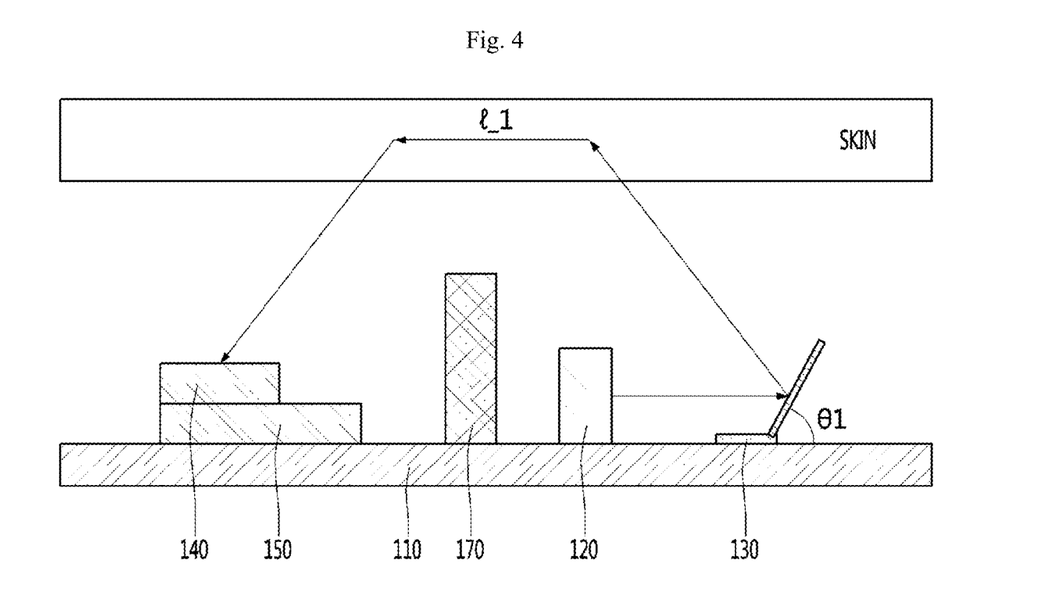
FIGS. 4 and 5 are views illustrating an optical path according to a reflection angle of a reflector according to the first embodiment of the present invention.
Figure 5:
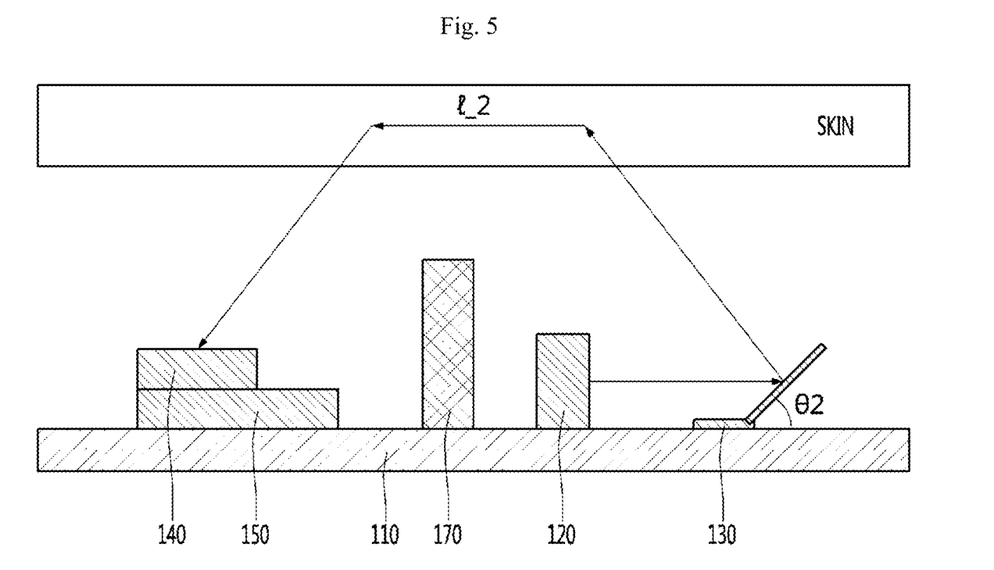

FIGS. 4 and 5 are views illustrating an optical path according to a reflection angle of a reflector according to the first embodiment of the present invention.

Referring to FIGS. 4 and 5, the reflector 130 may change an angle within a predetermined effective angle range. In addition, a path of light reflected to the measurement object changes according to the reflection angle of the reflector 130, and a state of light received via the light receiving unit 140 changes according to the optical path.

That is, as shown in FIG. 4, when the reflection angle of the reflector 130 is set to a first angle θ1, the path of light reflected via the reflector 130 is incident on the light receiving unit 140 via a first path 1_1.

In addition, as shown in FIG. 5, when the reflection angle of the reflector 130 is set to a second angle different from the first angle, the path of light reflected via the reflector 130 is incident on the light receiving unit 140 via a second path 1_2 different from the first path.

Further, a state of light incident through the first path and a state of light incident through the second path are shown to be different from each other.

Furthermore, an optimal path of light among the paths of light is not defined, and a difference occurs in a path of light showing an optimum signal state according to race, age, and sex.

Accordingly, the driving unit 150 determines whether the wearable device is worn on the human body, the driving unit 150 enters an angle setting mode of the reflector 130 when the wearable device is worn on the human body, and detects an optimum reflection angle of the reflector 130.

For this, the driving unit 150 changes the reflection angle of the reflector 130 within an effective range, and determines a state of an optical signal received via the light receiving unit 140 depending on each of the changed reflection angles.

Here, an effective range for the reflection angle of the reflector 130 may be set to 0 to 60 degrees, and the driving unit 150 finely adjusts the reflection angle within the effective range of 0 to 60 degrees, and confirms a signal-to-noise ratio (SNR) of an optical signal incident on the light receiving unit 140 depending on each of the adjusted reflection angles.

When the wearable device is initially worn on the human body, the driving unit 150 moves an effective range of the reflector 130, and accordingly, searches for a reflection angle at which the SNR of the optical signal reflected after the light reflected via the reflector 130 passes through the capillary blood vessels of a skin is the highest.

That is, the SNR of the optical signal is high, which means that quality of the original pulsating signal has been improved to a maximum, and accordingly, the driving unit 150 searches for a reflection angle of the reflector 130 whose SNR is the highest.

When the reflection angle is determined, the driving unit 150 fixes the reflection angle of the reflector 130 based on the determined reflection angle, and measures a bio-signal according to the fixed reflection angle.

In addition, when a user's movement and a predetermined time or re-wearing of the wearable device are performed, the driving unit 150 re-enters the above-described reflection angle setting mode, and determines again the optimum reflection angle corresponding to a current state.

Figure 6:
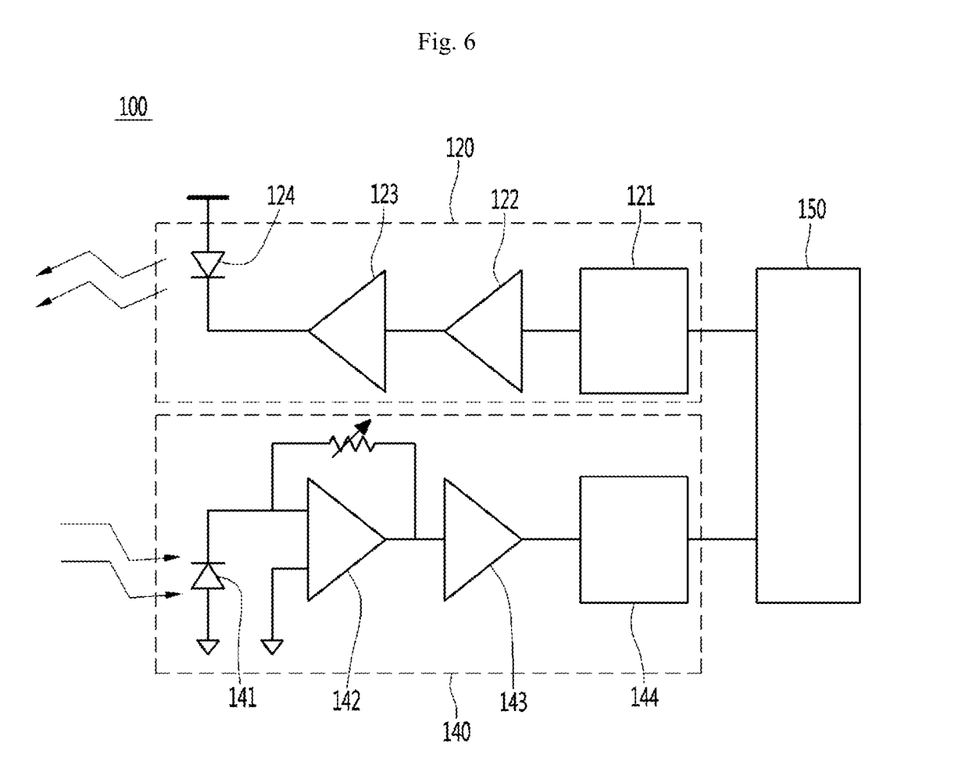
FIG. 6 is a view illustrating an internal configuration of a wearable device according to the first embodiment of the present invention.

FIG. 6 is a view illustrating an internal configuration of a wearable device according to the first embodiment of the present invention.

Referring to FIG. 6, a wearable device 100 includes a light emitting unit 120, a light receiving unit 140 and a driving unit 150.

The light emitting unit 120 generates light depending on a control signal of the driving unit 150.

The light emitting unit 120 may be roughly divided into a light emitting means for generating light and a driving means for driving the light emitting means.

The driving means of the light emitting unit 120 includes a digital-to-analog converter 121 configured to convert a digital signal output via the driving unit 150 into an analog signal, a first amplifier 122 configured to primarily amplify the signal converted via the digital-to-analog converter 121, and a second amplifier 123 configured to secondarily amplify the signal primarily amplified via the first amplifier 122.

Here, the digital-to-analog converter 121 converts the digital signal into an analog signal in order to set a current of a light emitting element 124.

In addition, the first and second amplifiers 122 and 123 are signal amplifying units for supplying an alternating current necessary for driving the light emitting element 124 to the light emitting element 124.

Further, the light emitting means of the light emitting unit 120 includes a light emitting element 124 for generating light according to a signal amplified via the second amplifier 123. The light emitting element 124 may be implemented as a light emitting diode (LED).

Furthermore, the light emitting element 124 may generate light having different wavelengths depending on a human body signal to be detected. That is, the light emitting element 124 may be a red light emitting diode, which generates light having a wavelength of 660 nm when the human body signal to be detected is a heart rate.

The light receiving unit 140 receives incident light including light reflected from a test object according to a light emitting operation of the light emitting unit 120.

The light receiving unit 140 includes a light receiving element 141 configured to receive the incident light, a first amplifier 142 configured to primarily amplify an optical signal incident via the light receiving element 141, a second amplifier 143 configured to secondarily amplify the signal primarily amplified via the first amplifier 142, and an analog-to-digital converter 144 configured to convert the signal secondarily amplified via the second amplifier 143 into a digital signal.

The light receiving element 141 receives light incident from the outside. At this point, the light receiving element 141 may be implemented with a photodiode (PD) or a transistor (TR).

In addition, the first amplifier 142 converts a weak photocurrent detected by the light receiving element 141 into a voltage and amplifies the voltage, which may be a transimpedance amplifier (TIA).

Further, the second amplifier 143 amplifies the voltage amplified via the first amplifier 142 to a voltage of sufficient magnitude to be processed by the analog-to-digital converter 144.

Furthermore, the analog-to-digital converter 144 converts an analog voltage to an equivalent digital voltage according to a specified sampling rate.

The driving unit 150 controls operations of the light emitting unit 120 and the light receiving unit 140.

In addition, the driving unit 150 detects a signal-to-noise ratio of an optical signal received via the light receiving unit 140 depending on operation modes of the light emitting unit 120 and the light receiving unit 140, and determines the optimum reflection angle of the reflector 130 according to the SNR of the detected optical signal.

At this point, the operation mode may include a normal operation mode and a reflection angle setting mode of the reflector 130.

The reflection angle setting mode is a mode for determining the optimum reflection angle of the reflector 130 according to a human body on which the wearable device 100 is worn by using the light emitting unit 120 and the light receiving unit 140.

Figure 7:
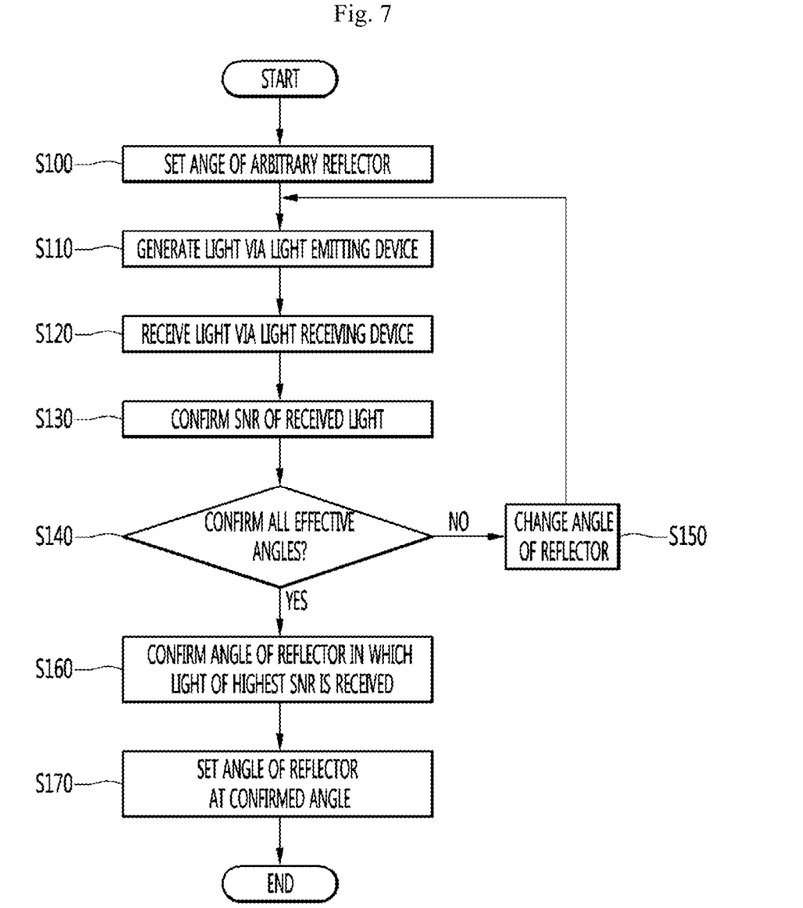
FIG. 7 is a flowchart for explaining an operation method of a wearable device according to the first embodiment of the present invention step by step.

FIG. 7 is a flowchart for explaining an operation method of a wearable device according to the first embodiment of the present invention step by step.

Referring to FIG. 7, the driving unit 150 determines whether the wearable device is worn on the human body. The driving unit 150 enters an angle setting mode of the reflector 130 when the human body is worn, and determines an optimum reflection angle of the reflector 130.

For this, the driving unit 150 changes the reflection angle of the reflector 130 within an effective range, and determines a state of an optical signal received via the light receiving unit 140 depending on each of the changed reflection angles.

That is, the driving unit 150 sets a specific reflection angle in the effective range at step S100.

When the specific reflection angle is set, the driving unit 150 controls operations of the light emitting unit 120 and the light receiving unit 140 at steps S110 and S120, and accordingly, confirms a SNR of the received light at step S130.

In addition, the driving unit 150 determines whether the signal-to-noise ratios for all of effective angles are confirmed or not at step S140.

Here, an effective range for the reflection angle of the reflector 130 may be set to 0 to 60 degrees, and the driving unit 150 finely adjusts the reflection angle within the effective range of 0 to 60 degrees, and confirms the signal to noise ratio (SNR) of an optical signal incident on the light receiving unit 140 depending on each of the adjusted reflection angles.

When all of the effective angles are not confirmed, the driving unit 150 changes the reflection angle of the reflector 130 at step S150, and accordingly, returns to the step S110.

In addition, when the SNR within all of effective angles is confirmed, the driving unit 150 searches for a reflection angle of which the SNR of the optical signal is the highest at step S160.

That is, the SNR of the optical signal is high, which means that quality of the original pulsating signal has been improved to a maximum, and accordingly, the driving unit 150 searches for a reflection angle of the reflector 130 of which SNR is the highest.

In addition, when the reflection angle is determined, the driving unit 150 fixes the reflection angle of the reflector 130 based on the determined reflection angle, and measures a bio-signal according to the fixed reflection angle at step S170.

Further, when a user's movement and a predetermined time or re-wearing of the wearable device are performed, the driving unit 150 re-enters the above-described reflection angle setting mode, and determines again the optimum reflection angle corresponding to a current state.

According to an embodiment of the present invention, a reflector using an optimized MEMS mirror is disposed between a light emitting element and a light receiving element, and thus noise reflected on a skin surface of a measurement object can be reduced.

In addition, according to an embodiment of the present invention, a reflector for reflecting light is disposed between a light emitting element and a light receiving element, and thus an optical path passing through a skin tissue can be minimized while reducing surface reflection.

Further, according to an embodiment of the present invention, a separate green light emitting element for measuring a heart rate can be removed by improving quality of a heartbeat signal on a wrist, and thus competitiveness of a unit price can be increased by lowering unit prices of products and volumes of the products can be miniaturized, accordingly.

Figure 8:
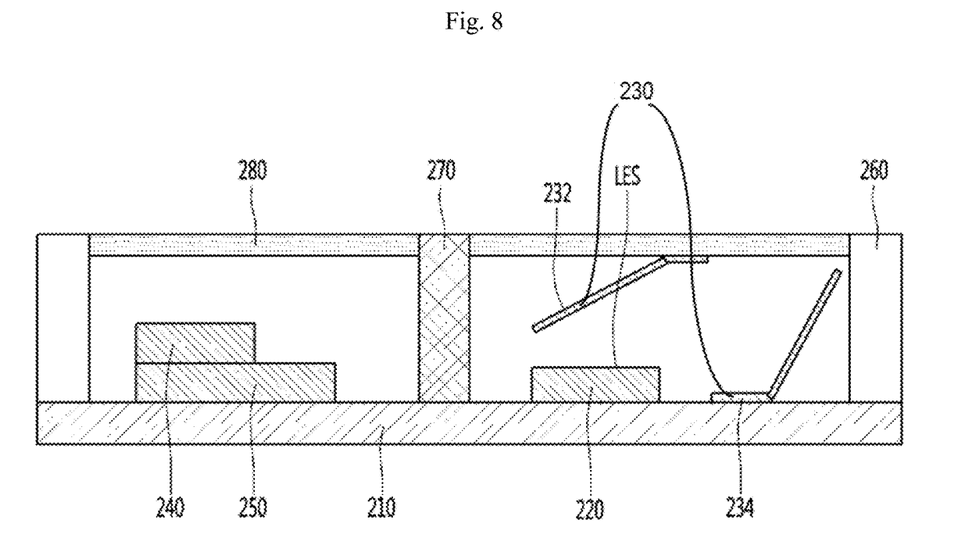
FIGS. 8 and 9 are views illustrating a structure of a wearable device according to a second embodiment of the present invention.
Figure 9:
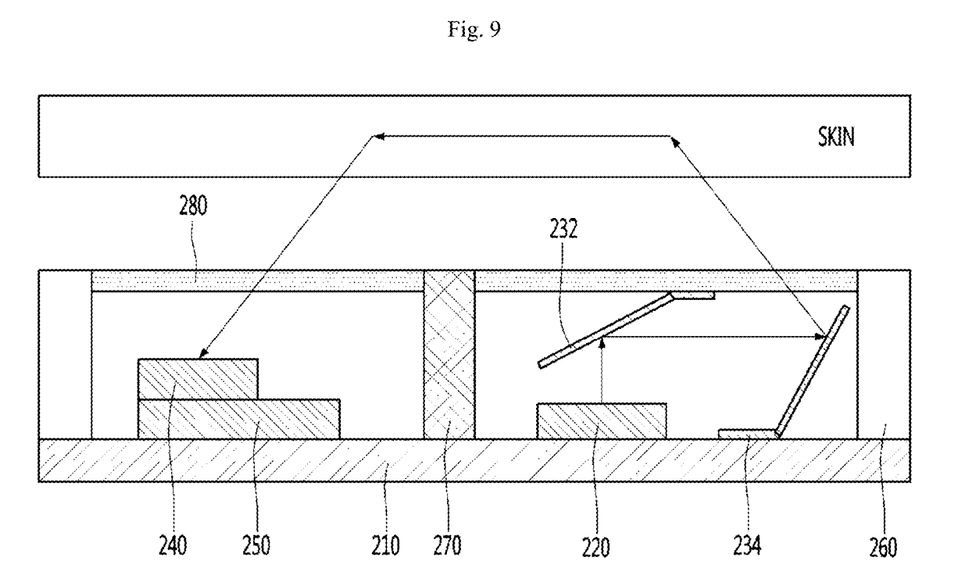

FIGS. 8 and 9 are views illustrating a structure of a wearable device according to a second embodiment of the present invention.

Referring to FIG. 8, a wearable device includes a substrate 210, a light emitting unit 220, a reflector 230, a light receiving unit 240, a driving unit 250, a structure 260, a partition wall 270 and an optical window 280. The reflector 230 includes a first reflector 232 and a second reflector 234.

The substrate 210 is a base substrate for mounting components constituting the wearable device.

That is, the substrate 210 may be a support substrate of the wearable device on which a single circuit pattern is formed, and may refer to a specific insulating layer on which any one of circuit pattern of a substrate having a plurality of laminated structures is formed.

The substrate 210 may be a thermosetting or thermoplastic polymer substrate, a ceramic substrate, an organic-inorganic composition material substrate, or a fiberglass immersion substrate, and when a polymer resin is included, an epoxy-based insulating resin may be included, otherwise, a polyimide-based resin may be included.

That is, the substrate 210 is a plate on which an electrical circuit capable of changing wirings is disposed and may include all of printing, a wiring plate, and an insulating substrate which are formed of an insulating material which is able to form a conductive pattern on a surface of the insulating substrate.

The substrate 210 may be rigid or flexible. For example, the substrate 210 may include glass or plastic. Specifically, the substrate 210 may include a chemically tempered/semi-tempered glass, such as soda lime glass, aluminosilicate glass, etc., a reinforced or flexible plastic such as polyimide (PI), polyethylene terephthalate (PET), propylene glycol (PPG), polycarbonate (PC), etc., or sapphire.

In addition, the substrate 210 may include an optically isotropic film. For example, the substrate 210 may include cyclic olefin copolymer (COC), cyclic olefin polymer (COP), optically isotropic polycarbonate (PC), optically isotropic polymethylmethacrylate (PMMA), etc.

Further, the substrate 210 may partially have a curved surface and may be bent. That is, the substrate 210 may partially have a flat surface and may partially have a curved surface and may be bent. Specifically, an end portion of the substrate 210 may have a curved surface and may be bent, or, may have a surface with a random curvature and may be bent or crooked.

Furthermore, the substrate 210 may be a flexible substrate having flexible characteristics.

In addition, the substrate 210 may be a curved or bent substrate. Here, the substrate 210 may form a wiring layout for electrical wirings, which connect circuit components based on a circuit design, and electrical conductors may be disposed thereon. Further, electrical components may be mounted on the insulating layer 110, and the insulating layer 110 may form wirings configured to connect the electrical components to make a circuit, and may mechanically fix the components besides functioning as electrically connecting the components.

A circuit pattern (not shown) electrically connected to the light emitting unit 220, the reflector 230, the light receiving unit 240, and the driving unit 250 to be described later is formed on a surface of the substrate 210.

The circuit pattern may be formed by a general process of manufacturing a PCB, such as an additive process, a subtractive process, a modified semi additive process (MSAP), a semi additive process (SAP), etc., and detailed descriptions thereof will be omitted herein.

The surface of the substrate 210 may be divided into a first region in which the light emitting unit 220 is mounted and a second region in which the light receiving unit 240 is mounted.

In addition, the partition wall 270 is disposed between the first and second regions, and the surface of the substrate 210 may be divided into the first region and the second region by the partition wall 270.

The partition wall 270 is disposed between the light emitting unit 220 and the light receiving unit 240 and inhibits light generated via the light emitting unit 220 from being directly incident on the light receiving unit 240.

In addition, the light emitting unit 220 and the reflector 230 are disposed in the first region of the substrate 210.

The light emitting unit 220 includes a light emitting element configured to generate light of a specific wavelength band according to a light emission control signal.

At this point, a light emitting surface (LES) of the light emitting unit 220 is disposed so as to be overlapped with the skin of a measurement object. For this, the light emitting unit 220 is disposed on the substrate 210 so that the LES is placed on an upper surface. Accordingly, the LES of the light emitting unit 220 is disposed at upper portion of the light emitting unit 220 so as to be overlapped with the skin of the measurement object.

The reflector 230 reflects the light generated via the light emitting unit 220 in a specific direction according to a predetermined angle.

That is, the reflector 230 includes a light reflection region, and the light reflection region is disposed to face the LES of the light emitting unit 220.

At this point, the reflector 230 includes a first reflector 232 and a second reflector 234, the first reflector 232 is configured such that a light reflection region is disposed so as to face the LES of the light emitting unit 220, and reflects the light emitted via the light emitting unit 120 to a first direction.

At this point, the light emitting unit 220 generates light substantially to the skin of the measurement object, and the first reflector 232 reflects the generated light to a first direction parallel to the skin of the measurement object.

In addition, a reflection region of the second reflector 234 is disposed so as to face the reflection region of the first reflector 232.

In addition, the second reflector 234 reflects light reflected via the first reflector 232 to the skin of the measurement object.

The first and second reflectors 232 and 234 are preferably a micro-electro-mechanical systems mirror (MEMS mirror).

In addition, the MEMS mirror may be divided into a mirror using an electrostatic force, a mirror using an electromagnetic force, a mirror using a piezoelectric force, a mirror using thermal deformation, and the like according to a driving method for driving the mirror. The mirror using the electrostatic force may be divided again into a parallel plate driving method and a comb-driving method.

In addition, each of the driving methods has advantages and disadvantages in comparison with other driving methods. In the driving methods, the comb-driving method, which is easy to manufacture and has a low power consumption, but is excellent in driving force, torque and maximum stroke, is most widely used.

Further, the above-described MEMS mirror may be slightly changed in angle within a predetermined effective angle range.

Accordingly, in the present invention, a reflection angle of the MEMS mirror constituting the first reflector 232 and second the reflector 234 is selectively changed so as to reflect the light generated via the light emitting unit 220 to an optimum optical path for the measurement object.

The structure 260 is a support structure for supporting the optical window 280.

The optical window 280 protects the light emitting unit 220, the light receiving unit 240, the first reflector 232, and the second reflector 234 from the outside.

The optical window 280 forms an optical path so that the light reflected via the first and second reflectors 232 and 234 is supplied to the outside (preferably, the skin of the measurement object), and allows light incident from the outside to be supplied to the light receiving unit 240.

Meanwhile, the driving unit 250 and the light receiving unit 240 are disposed in the second region of the substrate 210.

At this point, the driving unit 250 is disposed on the substrate 210, and the light receiving unit 240 is disposed on the driving unit 250.

The driving unit 250 may be a signal processing element for processing a signal received via the light receiving unit 240, and may be implemented as an application specific integrated circuit (ASIC).

The light receiving unit 240 is disposed on the driving unit 250. The light receiving unit 240 is disposed on the driving unit 250 such that a light incident surface faces to an upper portion.

Meanwhile, the driving unit 250 includes a controller (not shown), and controls the first and second reflectors 232 and 234 according to a state of wearing the wearable device, so that reflection angles of the first and second reflectors 232 and 234 are adjusted according to a human body on which the wearable device is worn.

That is, in the first embodiment of the present invention, the optimum reflection angle is determined by adjusting only the reflection angle of the reflector 130.

However, in the second embodiment, the optimum reflection angles of the first reflector and the second reflector are determined by adjusting the reflection angle according to a combination of the reflection angles of the first and second reflectors 232 and 234 as described above.

Figure 10:
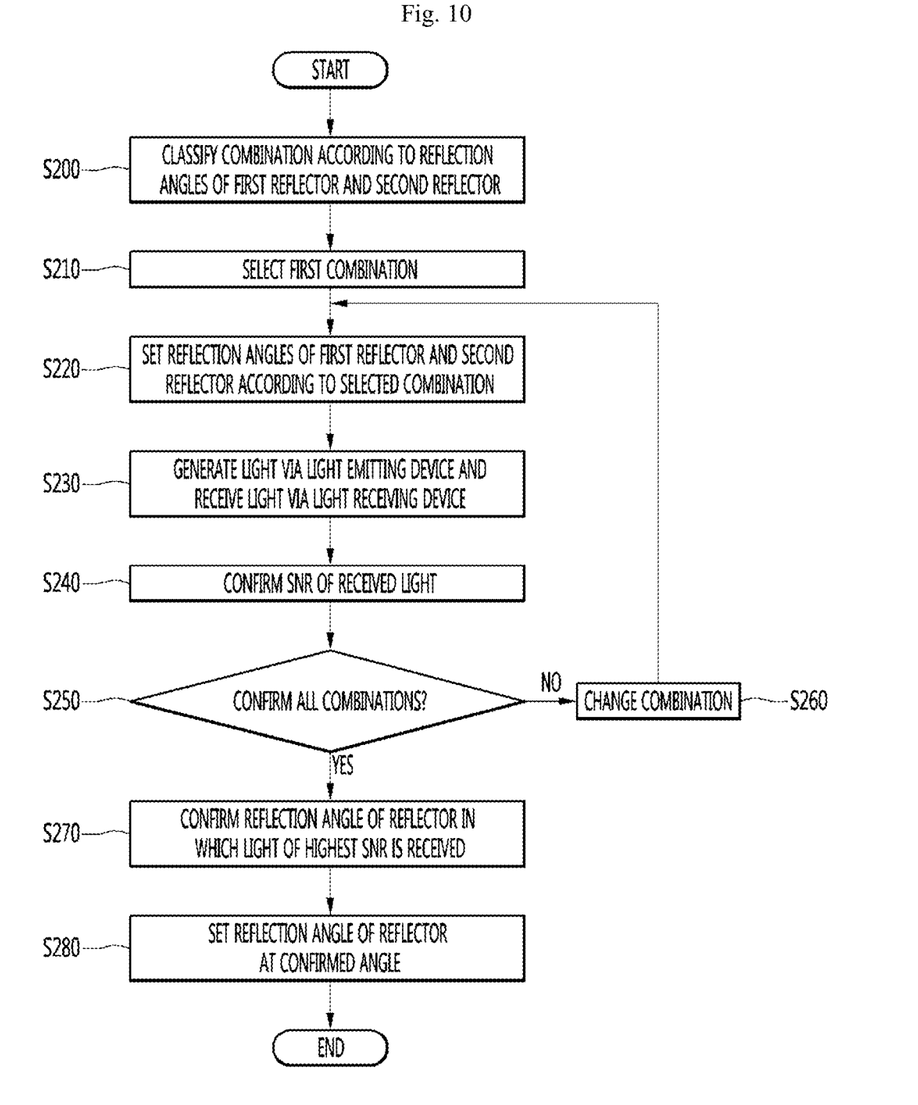
FIG. 10 is a flowchart for explaining an operation method of a wearable device according to the second embodiment of the present invention step by step.

FIG. 10 is a flowchart for explaining an operation method of a wearable device according to the second embodiment of the present invention step by step.

Referring to FIG. 10, the driving unit 250 determines whether the wearable device is worn on the human body. The driving unit 250 enters an angle setting mode of the first and second reflectors 232 and 234 when the human body is worn, and determines optimum reflection angles of the first and second reflectors 232 and 234.

For this, the driving unit 250 classifies combinations according to reflection angles of the first and second reflectors 230 at step S200, and selects a specific first combination among the classified combinations at step S210.

In addition, the driving unit 250 sets the reflection angles of the first and second reflectors 232 and 234 according to the selected combination at step S220.

When the specific reflection angles are set, the driving unit 250 controls operations of the light emitting unit 220 and the light receiving unit 240 at step S230, and accordingly, confirms a SNR of received light at step S240.

In addition, the driving unit 250 determines whether the signal-to-noise ratios for all combinations are confirmed or not at step S250.

Here, an effective range for the reflection angle of each of the first and second reflectors 232 and 234 may be set to 0 to 60 degrees, and the driving unit 250 confirms the signal-to-noise ratio (SNR) of an optical signal incident on the light receiving unit 240 depending on combinations of reflection angles within the effective range of 0 to 60 degrees, When all combinations are not confirmed, the driving unit 250 changes the reflection angles of the first and second reflectors 232 and 234 at step S260, and accordingly, returns to the step S220.

In addition, when the signal-to-noise ratio within all combinations is confirmed, the driving unit 250 searches for a combination of reflection angles of which the SNR of the optical signal is the highest at step S270.

That is, the SNR of the optical signal is high, which means that quality of the original pulsating signal has been improved to a maximum, and accordingly, the driving unit 150 searches for a combination of the reflection angles of the first and second reflectors 232 and 234 of which the SNR is the highest.

In addition, when the combination of the reflection angles is determined, the driving unit 250 fixes the reflection angles of the first and second reflectors 232 and 234 based on the reflection angles according to the determined combination, and measures a bio-signal according to the fixed reflection angles at step S280.

Further, when a user's movement and a predetermined time or re-wearing of the wearable device are performed, the driving unit 250 re-enters the above-described reflection angle setting mode, and determines again the optimum reflection angle corresponding to a current state.

According to an embodiment of the present invention, a reflector using an optimized MEMS mirror is disposed between a light emitting element and a light receiving element, and thus noise reflected on a skin surface of a measurement object can be reduced.

In addition, according to an embodiment of the present invention, a reflector for reflecting light is disposed between a light emitting element and a light receiving element, and thus an optical path passing through a skin tissue can be minimized while reducing surface reflection.

Further, according to an embodiment of the present invention, a separate green light emitting element for measuring a heart rate can be removed by improving quality of a heartbeat signal on a wrist, and thus competitiveness of a unit price can be increased by lowering unit prices of products and volumes of the products can be miniaturized, accordingly.

The invention claimed is:
1. A wearable device comprising:
    a substrate;
    a light emitter disposed on the substrate;
    a light receiver disposed on the substrate and spaced at a predetermined distance apart from the light emitter;
    a structure disposed on the substrate;
    an optical window disposed on the structure and configured to protect the light emitter and the light receiver;
    a first reflector disposed on the substrate adjacent to the light emitter;
    a second reflector disposed at a location facing a light emitting surface of the light emitter and disposed at a lower surface of the optical window; and
    a controller disposed on the substrate and configured to change reflection angles of the first and second reflectors,
    wherein the first reflector is in direct contact with the lower surface of the optical window;
    wherein the second reflector is in direct contact with a top surface of the substrate;
    wherein the first reflector is disposed on a light reflection path of the second reflector and reflects light reflected via the second reflector to a measurement object,
    wherein the light emitter generates light propagating in a first direction perpendicular to the measurement object, and
    wherein the first reflector reflects the light propagating in the first direction to a second direction in parallel to the measurement object, and the second reflector reflects the light reflected in the second direction to a third direction corresponding to the measurement object,
    wherein the controller is configured to classify combinations according to reflection angles of the first and second reflectors and determine reflection angles of the first and second reflectors within the classified combinations, and
    wherein the controller is configured to determine reflection angles of the first and second reflectors such that an optical path of light passing through the measurement object within the classified combinations is minimized,
    wherein the controller is configured to enter an angle setting mode of the first and second reflectors at time of initial wearing and time of re-wearing of the wearable device,
    wherein the controller is configured to detect a signal-to-noise ratio of an optical signal received via the light receiver in a state of entering the angle setting mode; and
    wherein the controller is configured to change the respective reflection angles of the first and the second reflectors to detect the signal-to-noise ratio of an optical signal received via the light receiver according to a combination of each of reflection angles, and set the respective reflection angles of the first and second reflectors based on a reflection angle corresponding to a greatest detected signal-to-noise ratio of the detected signal-to-noise ratios.

2. The wearable device of claim 1, wherein the light emitter is configured such that the light emitting surface is located at a first side surface and a second side surface facing the first side surface is in direct contact with the substrate and disposed on the substrate.

3. The wearable device of claim 1, wherein the first reflector includes a micro-electro-mechanical systems mirror (MEMS mirror).

4. The wearable device of claim 1, wherein the light emitter includes a red light emitting diode.

5. The wearable device of claim 1,
    wherein the light receiver is disposed on the controller.

6. The wearable device of claim 1, comprising
a partition wall disposed between the light emitter and the light receiver of the substrate and configured to divide an upper region of the substrate into a region in which the light emitter is disposed and a region in which the light receiver is disposed.

7. The wearable device of claim 1, wherein the light emitter comprises:
a digital-to-analog converter configured to convert a digital signal output via the controller into an analog signal,
a first amplifier configured to primarily amplify the signal converted via the digital-to-analog converter,
a second amplifier configured to secondarily amplify the signal primarily amplified via the first amplifier, and
a light emitting element configured to generate light according to the signal secondarily amplified via the second amplifier.

8. The wearable device of claim 1, wherein the light receiver comprises:
a light receiving element configured to receive light reflected from the measurement object,
a first amplifier configured to primarily amplify an optical signal incident via the light receiving element,
a second amplifier configured to secondarily amplify the signal primarily amplified via the first amplifier, and
an analog-to-digital converter configured to convert the signal secondarily amplified via the second amplifier into a digital signal.

\* \* \* \* \*